(12) United States Patent
Chen et al.

(10) Patent No.: US 11,149,004 B2
(45) Date of Patent: Oct. 19, 2021

(54) CRYSTALLINE FORM OF EB-1020, PROCESSES FOR PREPARATION AND USE THEREOF

(71) Applicant: Crystal Pharmaceutical (Suzhou) Co., Ltd., Jiangsu (CN)

(72) Inventors: Minhua Chen, Suzhou (CN); Yanfeng Zhang, Suzhou (CN); Xiaoting Zhai, Suzhou (CN); Xiaoyu Zhang, Suzhou (CN)

(73) Assignee: Crystal Pharmaceutical (Suzhou) Co., Ltd., Suzhou (CN)

( * ) Notice: Subject to any disclaimer, the term of this patent is extended or adjusted under 35 U.S.C. 154(b) by 0 days.

(21) Appl. No.: 16/771,373

(22) PCT Filed: Oct. 11, 2018

(86) PCT No.: PCT/CN2018/109908
§ 371 (c)(1),
(2) Date: Jun. 10, 2020

(87) PCT Pub. No.: WO2019/114394
PCT Pub. Date: Jun. 20, 2019

(65) Prior Publication Data
US 2021/0179558 A1 Jun. 17, 2021

(30) Foreign Application Priority Data
Dec. 11, 2017 (CN) .......................... 201711308926.7
Aug. 17, 2018 (CN) .......................... 201810942641.7

(51) Int. Cl.
*C07D 209/52* (2006.01)
(52) U.S. Cl.
CPC ........ *C07D 209/52* (2013.01); *C07B 2200/13* (2013.01)
(58) Field of Classification Search
None
See application file for complete search history.

(56) References Cited

U.S. PATENT DOCUMENTS

2016/0368871 A1* 12/2016 McKinney .............. A61P 25/00

FOREIGN PATENT DOCUMENTS

WO 2016/205762 A1 12/2016

OTHER PUBLICATIONS

International Search Report and Written Opinion for Application No. PCT/CN2018/109908, dated Jan. 9, 2019, 8 pages.

* cited by examiner

*Primary Examiner* — Sudhakar Katakam
*Assistant Examiner* — Jennifer C Sawyer
(74) *Attorney, Agent, or Firm* — McCarter & English, LLP; Steven G. Davis; Wei Song (57) ABSTRACT

The present disclosure relates to a crystalline form of compound I and processes for preparation thereof. The present disclosure also relates to a pharmaceutical composition containing the crystalline form, use of the crystalline form for preparing serotonin, norepinephrine and dopamine triple reuptake inhibitors drugs, and/or use of the crystalline form for preparing drugs treating nervous system disorders. The crystalline form of the present disclosure has one or more improved properties compared with prior art and has significant values for future drug optimization and development.

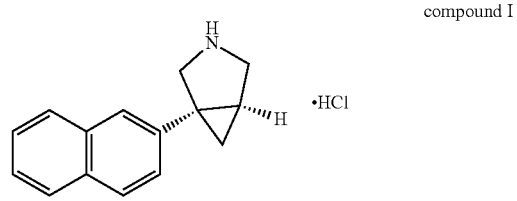

compound I

10 Claims, 6 Drawing Sheets

CRYSTALLINE FORM OF EB-1020, PROCESSES FOR PREPARATION AND USE THEREOF

CROSS-REFERENCE TO RELATED APPLICATIONS

This application is a U.S. national stage filing, under 35 U.S.C. § 371(c), of International Application No. PCT/CN2018/109908, filed on Oct. 11, 2018, which claims priority to Chinese Patent Application No. 201711308926.7, filed on Dec. 11, 2017, and Chinese Patent Application No. 201810942641.7, filed on Aug. 17, 2018. The entire contents of each of the aforementioned applications are incorporated herein by reference.

TECHNICAL FIELD

The present disclosure relates to the field of pharmaceutical chemistry, particularly relates to a crystalline form of EB-1020 and processes for preparation and use thereof.

BACKGROUND

Norepinephrine, serotonin and dopamine are three biogenic amines that relate to multiple neurological disorders. Inhibiting the reuptake of norepinephrine, dopamine and serotonin is a potential treatment for central nervous system disorders. EB-1020 (Centanafadine Hydrochloride) is a triple reuptake inhibitor that inhibits the reuptake of norepinephrine, serotonin and dopamine. Researches show that EB-1020 has potential palliative or curative effect for nervous system disorders, especially attention deficit hyperactivity disorder (ADHD).

The chemical name of EB-1020 is (1R,5S)-1-(naphthalen-2-yl)-3-azabicyclo[3.1.0]hexane hydrochloride (hereinafter referred to as "compound I"), and the structure is shown as follows:

compound I

The prior art WO2016205762A disclosed Form A, Form B and Form C of EB-1020. According to paragraph [00232] of specification in WO2016205762A, Form C converted to a mixture of Form A and Form B after being stored under the condition of 40° C./75% RH (Relative Humidity) for two weeks. The inventors have discovered through research that Form C converted to Form A after being stored at room temperature for a month. It indicates that Form C has poor stability, resulting in high risk of drug development.

Paragraph [00172] of specification in WO2016205762A disclosed that there are peaks of Form A in the XRPD pattern of Form B. It shows that Form A can form easily in Form B, and Form B is difficult to be purified, thus is not conducive to large-scale production and application in drug product. According to paragraph [00179] of specification in WO2016205762A, prior art Form A and Form B are needle-like crystals. Needle-like crystals are not beneficial to tableting because of poor compressibility and flowability. Furthermore, needle-like crystals usually carry static electricity, so it is difficult to form drug product.

There is still a need in the art to find excellent crystalline forms suitable for drugs by systematic and comprehensive crystal screening of compound I. The inventors of the present disclosure have discovered crystalline form CS1 of EB-1020 with superior properties. Crystalline form CS1 of EB-1020 in the present disclosure has advantages in at least one aspect of stability, melting point, solubility, in vitro and in vivo dissolution, hygroscopicity, bioavailability, adhesiveness, compressibility, flowability, processability, purification ability, formulation production, etc. In particular, it has good stability, high solubility, good processability in formulation process, which provides a new and better choice for the development of compound I and is of great significance.

SUMMARY

The main objective of the present disclosure is to provide a crystalline form of compound I, processes for preparation and use thereof.

According to the objective of the present disclosure, crystalline form CS1 of compound I is provided (hereinafter referred to as Form CS1).

According to one aspect of the present disclosure, the X-ray powder diffraction pattern of Form CS1 shows characteristic peaks at 2theta values of 21.0°±0.2°, 25.3°±0.2°, 14.1°±0.2° and 16.1°±0.2° using CuKα radiation.

Further, the X-ray powder diffraction pattern of Form CS1 shows one or two characteristic peaks at 2theta values of 17.8°±0.2° and 20.6°±0.2°. Preferably, the X-ray powder diffraction pattern of Form CS1 shows two characteristic peaks at 2theta values of 17.8°±0.2° and 20.6°±0.2°.

Further, the X-ray powder diffraction pattern of Form CS1 shows one or two characteristic peaks at 2theta values of 18.3°±0.2° and 19.4°±0.2°. Preferably, the X-ray powder diffraction pattern of Form CS1 shows two characteristic peaks at 2theta values of 18.3°±0.2° and 19.4°±0.2°.

According to another aspect of the present disclosure, the X-ray powder diffraction pattern of Form CS1 shows three or four or five or six or seven or eight or nine or ten characteristic peaks at 2theta values of 21.0°±0.2°, 25.3°±0.2°, 13.9°±0.2°, 14.1°±0.2°, 16.1°±0.2°, 17.8°±0.2°, 20.6°±0.2°, 18.3°±0.2°, 19.4°±0.2° and 21.3°±0.2°.

Figure 1:
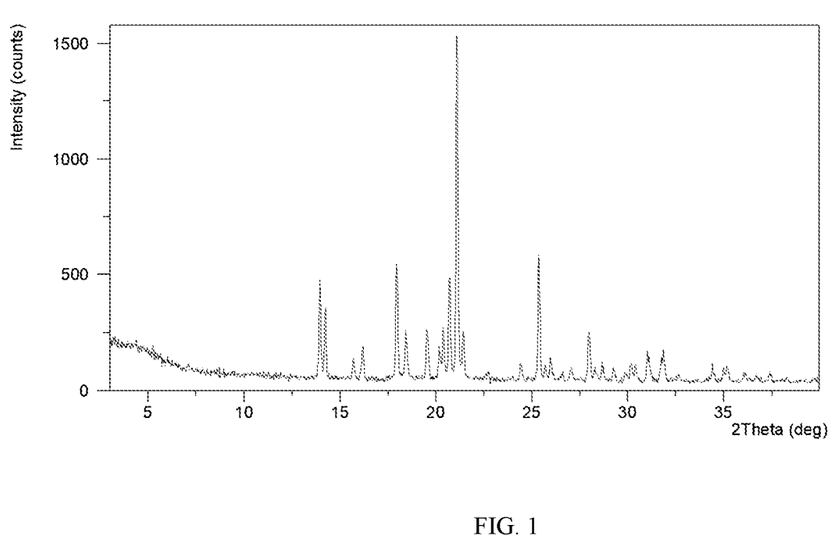
FIG. 1 shows an XRPD pattern of Form CS1 in Example 1.

Without any limitation being implied, the X-ray powder diffraction pattern of Form CS1 is as depicted in FIG. 1.

According to the objective of the present disclosure, a process for preparing Form CS1 is also provided, wherein the process comprises:

Weighing certain amount of compound I, melting by heating under an inert atmosphere, and cooling to obtain Form CS1.

Further, said heating and melting temperature is 248±2° C.

According to the objective of the present disclosure, a pharmaceutical composition is also provided. Said pharmaceutical composition comprises a therapeutically effective amount of Form CS1 and pharmaceutically acceptable carriers, diluents or excipients.

Further, Form CS1 can be used for preparing serotonin, norepinephrine and dopamine triple reuptake inhibitors drugs.

Further, Form CS1 can be used for preparing drugs treating nervous system disorders.

Furthermore, Form CS1 can be used for preparing drugs treating attention deficit hyperactivity disorder.

Form CS1 of the present disclosure has the following advantages:

(1) The crystalline form of the present disclosure has good physicochemical stability.

Form CS1 of the present disclosure remains unchanged for at least 6 weeks after being stored under the conditions of 25° C./60% RH (open) and 40° C./75% RH (open). Preferably, Form CS1 remains unchanged for at least 4 months. Form CS1 remains unchanged for at least one week when being stored under the condition of 80° C. The chemical purity of Form CS1 is above 99%, preferably above 99.9%, and remains substantially unchanged during storage. Moreover, Form CS1 remains unchanged after Form CS1 drug substance is compressed into tablets under different pressures, indicating that Form CS1 has good physical stability.

Form CS1 drug substance has good physicochemical stability. Form CS1 will not convert to other crystalline forms during storage and formulation processes. Furthermore, the chemical purity of Form CS1 remains substantially unchanged, ensuring consistent and controllable quality of the drug substance and drug product.

(2) Compared with prior art, Form CS1 of the present disclosure has higher solubility. In FeSSIF (Fed state simulated intestinal fluids), the solubility of Form CS1 is almost twice as much as that of prior art Form A and Form B.

Higher solubility is beneficial to improve bioavailability of drugs, thus improving drugability and efficacy. In addition, drug dose reduction without affecting efficacy is possible due to higher solubility, thereby reducing the side effects of drugs and improving drug safety.

(3) Compared with prior art, Form CS1 of the present disclosure has better mechanical stability. Form CS1 of the present disclosure remains unchanged after grinding and has little change in crystallinity, therefore, Form CS1 has good grinding stability. Form A shows obvious decrease of crystallinity after grinding and Form B partially converts to Form A after grinding. Grinding and pulverization are often required in formulation process. Good grinding stability of Form CS1 can reduce the risk of crystallinity change and crystal transformation in drug substance during formulation process.

(4) Form CS1 has good stability in drug product. Form CS1 of the present disclosure is mixed with excipients to make a drug product. When being stored under the conditions of 25° C./60% RH and 40° C./75% RH, Form CS1 remains unchanged for at least one month and has little change in purity during storage.

Crystal transformation in drug product may lead to changes in the absorption of drugs, and even cause toxicity and side effects. Form CS1 has good chemical and physical stability in drug product, ensuring consistent and controllable quality of the drug substance and drug product, minimizing toxicity increase of the drug caused by crystal transformation to the greatest extent, and ensuring the drug efficacy.

(5) Form CS1 of the present disclosure has good in vitro dissolution and dissolution rate. In pH=5.0 acetic acid buffer solution, the cumulative dissolution of drug product containing Form CS1 at 60 minutes is up to 95.29%.

Crystalline form difference can affect drug product's in vivo dissolution rate, which directly affects drug's in vivo absorption, distribution, excretion and metabolism, and finally leads to difference in clinical efficacy due to different bioavailability. Dissolution and dissolution rate are important prerequisites for drug absorption. Good in vitro dissolution leads to higher in vivo absorption, better in vivo exposure, thereby improving drug's bioavailability and efficacy. High dissolution rate is beneficial for the drug to achieve peak concentration in plasma quickly after administration, thus ensuring rapid drug action.

Furthermore, Form CS1 of the present disclosure also have the following advantages:

(1) Form CS1 of the present disclosure is a spherical or short rod-like crystal instead of a needle-like crystal. Form CS1 has better flowability and is beneficial to process and preparation of drug product. Form A and Form B are needle-like crystals, and have poor compressibility and flowability, which is not beneficial for tableting of drug product.

(2) Form CS1 of the present disclosure has better compressibility. Failure in hardness/friability test and tablet crack issue can be avoided due to better compressibility, making the process of drug product more reliable, improving product appearance and product quality. Better compressibility can increase the compression rate, thus further increases the efficiency of process and reduces the cost of compressibility improving excipients.

(3) Form CS1 of the present disclosure shows superior adhesiveness. Adhesiveness evaluation results show that adhesion quantity of Form CS1 is low and Form CS1 has low adhesiveness. Due to low adhesiveness of Form CS1, adhesion to roller and tooling during dry-granulation and compression process can be reduced, which is also beneficial to improve product appearance and weight variation. In addition, low adhesiveness of Form CS1 can reduce the agglomeration of drug substance, which is beneficial to the dispersion of drug substance, reduces the adhesion between materials and instruments, and improves the blend uniformity and content uniformity of drug product. In the present disclosure, "crystal" or "crystalline form" refers to the crystal or the crystalline form being identified by the X-ray diffraction pattern shown herein. Those skilled in the art are able to understand that physicochemical properties discussed herein can be characterized. The experimental errors depend on the instrument conditions, the preparation of sample and the purity of samples. In particular, those skilled in the art generally know that the X-ray diffraction pattern typically varies with the experimental conditions. It is necessary to point out that, the relative intensity of the diffraction peaks in the X-ray diffraction pattern may also vary with the experimental conditions; therefore, the order of the diffraction peak intensities cannot be regarded as the sole or decisive factor. In fact, the relative intensity of the diffraction peaks in the X-ray powder diffraction pattern is related to the preferred orientation of the crystals, and the diffraction peak intensities shown herein are illustrative and identical diffraction peak intensities are not required. In addition, the experimental error of the diffraction peak position is usually 5% or less, and the error of these positions should also be taken into account. An error of ±0.2° is usually allowed. In addition, due to experimental factors such as sample thickness, the overall offset of the diffraction peak is caused, and a certain offset is usually allowed. Thus, it will be understood by those skilled in the art that a crystalline form of the present disclosure is not necessarily to have exactly the same X-ray diffraction pattern of the example shown herein. Any crystalline forms whose X-ray diffraction patterns have the same or similar characteristic peaks should be within the scope of the present disclosure. Those skilled in the art can compare the patterns shown in the present disclosure with that of an unknown crystalline form in order to identify whether these two groups of patterns reflect the same or different crystalline forms.

In some embodiments, Form CS1 of the present disclosure is pure and substantially free of any other crystalline forms. In the present disclosure, the term "substantially free" when used to describe a novel crystalline form, it means that the content of other crystalline forms in the novel crystalline form is less than 20% (w/w), specifically less than 10% (w/w), more specifically less than 5% (w/w) and further more specifically less than 1% (w/w).

It should be noted that the number and the number range should not be understood as the number or number range themselves only. It should be understood by those skilled in the art that the specific number can be shifted at specific technical environment without departing from the spirit and principle of the present disclosure. In the present disclosure, the shift ranges expected by those skilled in the art is represented by the term "about".

DETAILED DESCRIPTION

The present disclosure is further illustrated by the following examples which describe the preparation and use of the crystalline form of the present disclosure in detail. It is obvious to those skilled in the art that many changes in the materials and methods can be accomplished without departing from the scope of the present disclosure.

The abbreviations used in the present disclosure are explained as follows:
XRPD: X-Ray Powder Diffraction
DSC: Differential Scanning calorimetry
TGA: Thermo Gravimetric Analysis
DVS: Dynamic Vapor Sorption
$^1$H NMR: Proton Nuclear Magnetic Resonance
HPLC: High Performance Liquid Chromatography
Instruments and Methods Used for Data Collection:
X-ray powder diffraction patterns in the present disclosure were acquired by a Panalytical Empyrean X-ray powder diffractometer. The parameters of the X-ray powder diffraction method of the present disclosure are as follows:
X-ray Reflection: Cu, Kα
Kα1 (Å): 1.540598; Kα2 (Å): 1.544426
Kα2/Kα1 intensity ratio: 0.50
Voltage: 45 (kV)
Current: 40 (mA)
Scan range: from 3.0 degree to 40.0 degree
Differential scanning calorimetry (DSC) data in the present disclosure were acquired by a TA Q2000. The parameters of the DSC method of the present disclosure are as follows:
Heating rate: 10° C./min
Purge gas: nitrogen
Thermo gravimetric analysis (TGA) data in the present disclosure were acquired by a TA Q500. The parameters of the TGA method of the present disclosure are as follows:
Heating rate: 10° C./min
Purge gas: nitrogen
Dynamic Vapor Sorption (DVS) data in the present disclosure were collected via an SMS (Surface Measurement Systems Ltd.) intrinsic DVS instrument. The Parameters for DVS test are as follows:
Temperature: 25° C.
Gas and flow rate: $N_2$, 200 mL/min
dm/dt: 0.002%/min
RH range: 0% RH to 95% RH
Ion Chromatography (IC) data were collected from a Thermo Fisher ICS-1100. The method parameters are as follows:
1. Column: IonPac AS18 (4×250 mm)
2. Eluent: 25 mM NaOH
3. Flow rate: 1.0 mL/min
4. Injection Volume: 25
5. Column Temperature: 35° C.
6. Suppressor current: 80 mA
7. Running Time: 6 min
High Performance Liquid Chromatography (HPLC) data for purity test in the present disclosure were collected from an Agilent 1260 with Diode Array Detector (DAD). The method parameters are as follows:
Column: L016 #Waters Xbridge C18, 150×4.6 mm, 5 μm
Mobile Phase: A: 25 mM $KH_2PO_4$ in $H_2O$, pH=2.5
B: acetonitrile
Gradient:

| Time (min) | % B |
|---|---|
| 0.0 | 10 |
| 20.0 | 40 |
| 30.0 | 80 |
| 35.0 | 80 |
| 35.1 | 10 |
| 40.0 | 10 |

Flow rate: 1.0 mL/min
Injection Volume: 5
Detection wavelength: 226 nm, reference wavelength is 500 nm
Column Temperature: 40° C.
Diluent: Water: Acetonitrile (V:V)=1:1

High Performance Liquid Chromatography (HPLC) data for solubility test in the present disclosure were collected from an Agilent 1260 with Diode Array Detector (DAD). The method parameters are as follows:
Column: L016 #Waters Xbridge C18, 150×4.6 mm, 5 μm
Mobile Phase: A: 25 mM $KH_2PO_4$ in $H_2O$, pH=2.5
  B: acetonitrile
Gradient:

| Time (min) | % B |
|---|---|
| 0.0 | 20 |
| 10.0 | 40 |
| 11.0 | 80 |
| 15.0 | 80 |
| 15.1 | 20 |
| 20.0 | 20 |

Flow rate: 1.0 mL/min
Injection Volume: 5 μL
Detection wavelength: 226 nm
Column Temperature: 40° C.
Diluent: $H_2O$: Acetonitrile (V:V)=1:1

Proton nuclear magnetic resonance ($^1$H NMR) spectrum data were collected from a Bruker Avance II DMX 400M HZ NMR spectrometer. 1-5 mg of sample was weighed and dissolved in 0.5 mL of deuterated dimethyl sulfoxide to obtain a solution with a concentration of 2-10 mg/mL.

Unless otherwise specified, the following examples were conducted at room temperature. Said "room temperature" is not a specific value, and refers to 10-30° C.

According to the present disclosure, compound I used as a raw material is solid (crystalline or amorphous), semisolid, wax or oil. Preferably, compound I used as a raw material is a solid.

EB-1020 used in the following examples were prepared by known methods in the prior art, for example, the preparation method disclosed in WO2016205762A.

Example 1: Preparation of Form CS1

Approximately 15 mg of raw material of compound I was weighed and placed in a DSC pan. The raw material was melted by heating to 248° C. at a rate of 10° C./min and then cooled to room temperature to obtain a white solid.

The obtained solid was confirmed to be Form CS1. The XRPD pattern is as depicted in FIG. 1, and the XRPD data are listed in Table 1.

Figure 2:
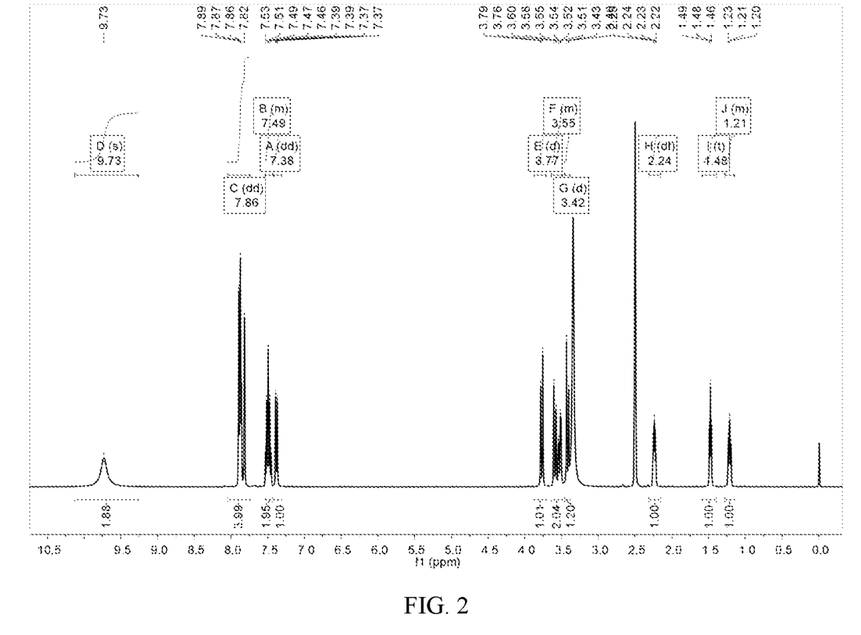
FIG. 2 shows a $^1$HNMR spectrum of Form CS1 in Example 1.

The $^1$H NMR spectrum of Form CS1 is substantially as depicted in FIG. 2, and the corresponding data are: $^1$H NMR (400 MHz, $d_6$-DMSO) δ 9.73 (s, 2H), 7.86 (dd, J=18.0, 12.1 Hz, 4H), 7.53-7.43 (m, 2H), 7.38 (dd, J=8.6, 1.2 Hz, 1H), 3.77 (d, J=11.1 Hz, 1H), 3.64-3.49 (m, 2H), 3.42 (d, J=11.2 Hz, 1H), 2.24 (dt, J=8.3, 4.2 Hz, 1H), 1.48 (t, J=5.3 Hz, 1H), 1.28-1.15 (m, 1H).

Figure 3:
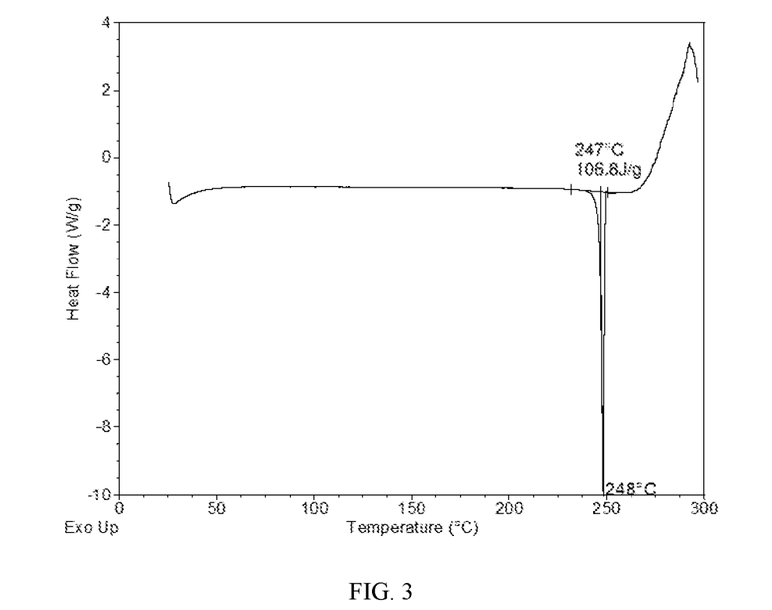
FIG. 3 shows a DSC curve of Form CS1 in Example 1.

The DSC curve of Form CS1 shows an endothermic peak at around 247° C. (onset temperature) corresponding to the melting process, which is substantially as depicted in FIG. 3.

Figure 4:
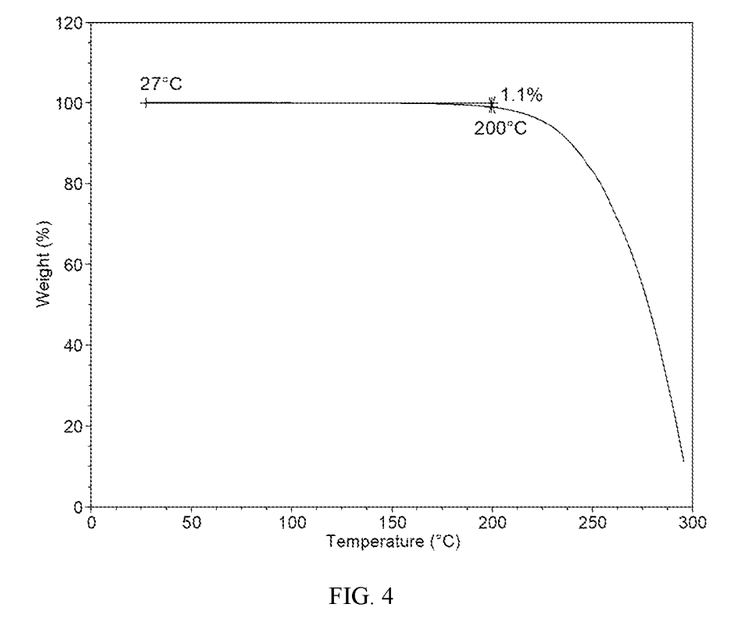
FIG. 4 shows a TGA curve of Form CS1 in Example 1.

The TGA curve of Form CS1 shows about 1.1% weight loss when heated to 200° C., which is substantially as depicted in FIG. 4.

The mole ratio of EB-1020 freebase and chloride ion in Form CS1 was determined by IC. The test results are listed in Table 2, which show that Form CS1 is a monohydrochloride.

TABLE 1

| 2 Theta | d spacing | Intensity % |
|---|---|---|
| 13.86 | 6.39 | 28.78 |
| 14.12 | 6.27 | 21.15 |
| 15.62 | 5.67 | 5.26 |
| 16.11 | 5.50 | 8.54 |
| 17.84 | 4.97 | 34.58 |
| 18.32 | 4.84 | 14.82 |
| 19.44 | 4.57 | 13.74 |
| 20.06 | 4.43 | 9.30 |
| 20.28 | 4.38 | 15.31 |
| 20.60 | 4.31 | 28.24 |
| 20.98 | 4.23 | 100.00 |
| 21.33 | 4.17 | 14.90 |
| 24.31 | 3.66 | 5.19 |
| 25.25 | 3.53 | 36.57 |
| 25.58 | 3.48 | 4.66 |
| 25.87 | 3.44 | 6.17 |
| 26.94 | 3.31 | 4.48 |
| 27.87 | 3.20 | 14.89 |
| 28.18 | 3.17 | 3.27 |
| 28.56 | 3.13 | 5.59 |
| 29.19 | 3.06 | 2.47 |
| 29.78 | 3.00 | 2.35 |
| 30.03 | 2.98 | 4.03 |
| 30.90 | 2.89 | 8.31 |
| 31.70 | 2.82 | 5.88 |
| 32.56 | 2.75 | 2.87 |
| 34.30 | 2.61 | 5.47 |
| 35.11 | 2.56 | 3.46 |

TABLE 2

| Solid form | Content of freebase (mol/g) | Content of chloride ion (mol/g) | Mole ratio of freebase/chloride ion |
|---|---|---|---|
| Form CS1 | $4.07 \times 10^{-3}$ | $3.99 \times 10^{-3}$ | 1:1 |

Example 2: Stability of Form CS1

A certain amount of Form CS1 were stored under different conditions of 25° C./60% RH (open) and 40° C./75% RH (open) for 6 weeks and 80° C. (open) for 1 week. Crystalline form and chemical purity were checked by XRPD and HPLC, respectively. The results are shown in Table 3 and Table 4.

TABLE 3

Figure 5:
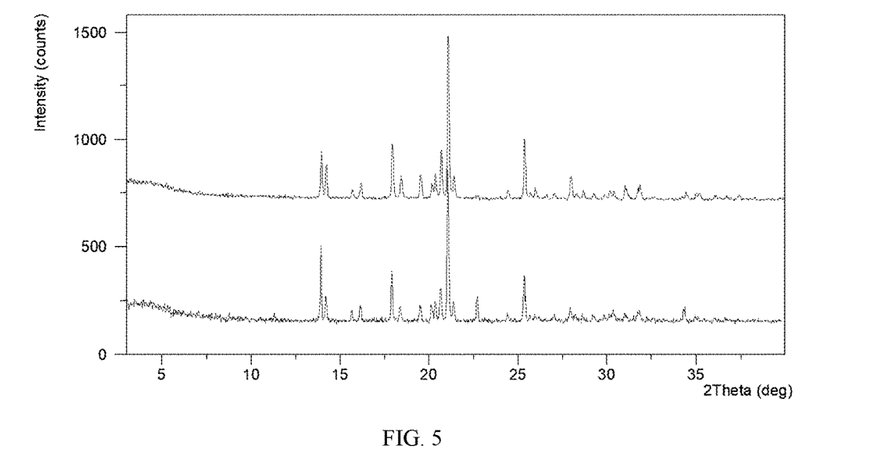
FIG. 5 shows an XRPD pattern overlay of Form CS1 before and after being stored under 25° C./60% RH (top: before storage, bottom: after storage).
Figure 6:
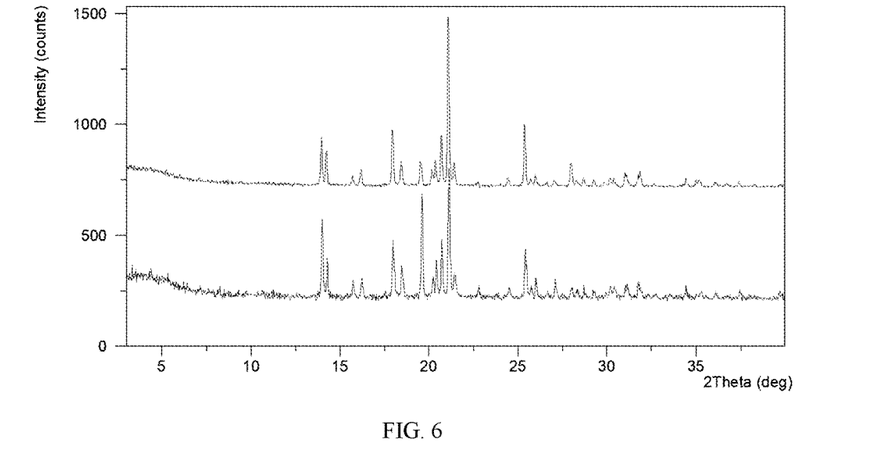
FIG. 6 shows an XRPD pattern overlay of Form CS1 before and after being stored under 40° C./75% RH (top: before storage, bottom: after storage).
Figure 7:
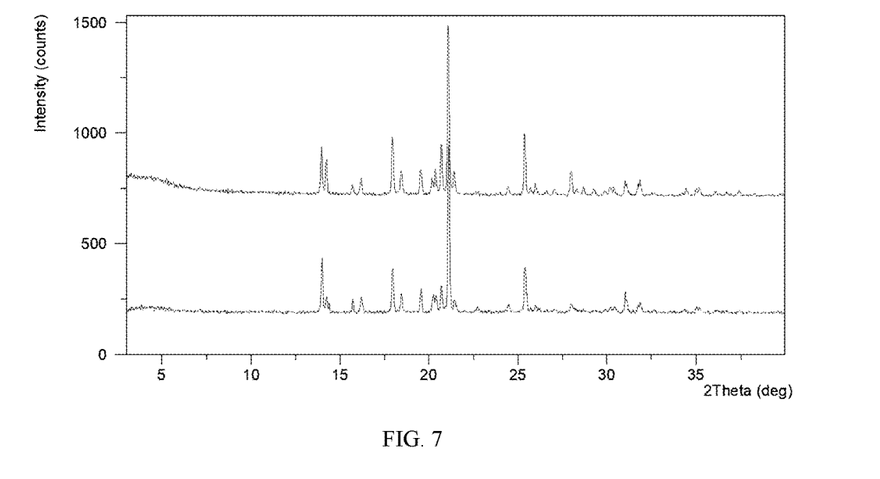
FIG. 7 shows an XRPD pattern overlay of Form CS1 before and after being stored under 80° C. (top: before storage, bottom: after storage).

| Initial solid form | Condition | Time | Solid form after storage |
|---|---|---|---|
| Form CS1 (FIG. 5, top) | 25° C./60% RH | 6 weeks | Form CS1 (FIG. 5, bottom) |
| Form CS1 (FIG. 6, top) | 40° C./75% RH | 6 weeks | Form CS1 (FIG. 6, bottom) |
| Form CS1 (FIG. 7, top) | 80° C. | 1 week | Form CS1 (FIG. 7, bottom) |

TABLE 4

| Condition | Purity after 1 Week | Purity after 2 Weeks | Purity after 6 Weeks |
|---|---|---|---|
| 25° C./60% RH | 99.93% | 99.95% | 99.94% |
| 40° C./75% RH | 99.95% | 99.95% | 99.97% |
| 80° C. | 99.82% | — | — |

The results show that Form CS1 remained unchanged for at least 6 weeks when being stored under the conditions of 25° C./60% RH and 40° C./75% RH. Form CS1 remained unchanged for at least 1 week when being stored under stress condition of 80° C. Furthermore, the chemical purity of Form CS1 remained substantially unchanged during storage. It shows that Form CS1 has good physicochemical stability.

Example 3: Grinding Stability of Form CS1, Prior Art Form a and Form B

Figure 8:
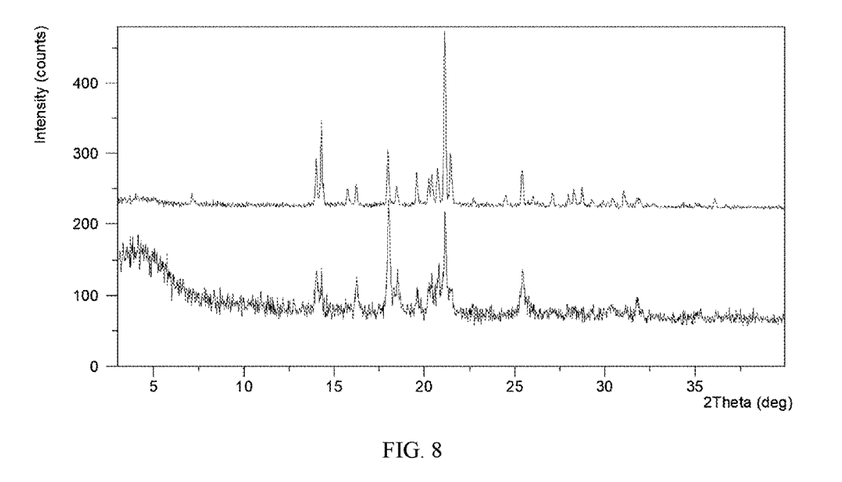
FIG. 8 shows an XRPD pattern overlay of Form CS1 before and after grinding (top: before grinding, bottom: after grinding).
Figure 9:
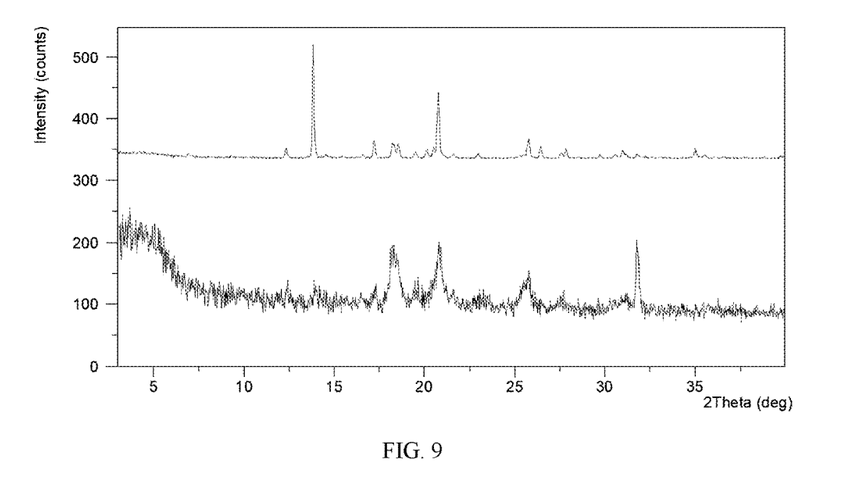
FIG. 9 shows an XRPD pattern overlay of prior art Form A before and after grinding (top: before grinding, bottom: after grinding).
Figure 10:
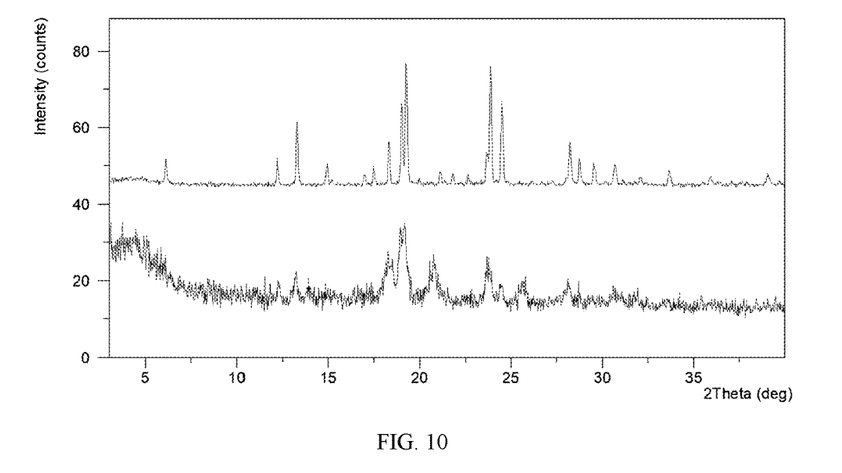
FIG. 10 shows an XRPD pattern overlay of prior art Form B before and after grinding (top: before grinding, bottom: after grinding).

A certain amount of Form CS1, prior art Form A and Form B were ground manually for 5 minutes in a mortar. The XRPD patterns of Form CS1 before and after grinding are as depicted in FIG. 8 (top: before grinding; bottom: after grinding). The XRPD patterns of prior art Form A before and after grinding are as depicted in FIG. 9 (top: before grinding; bottom: after grinding). The XRPD patterns of prior art Form B before and after grinding are as depicted in FIG. 10 (top: before grinding; bottom: after grinding).

The results show that the crystalline form of Form CS1 remained unchanged after grinding, and the crystallinity remained substantially unchanged. Form CS1 has good grinding stability. However, the crystallinity of prior art Form A decreased obviously after grinding, and a large amount of amorphous solid appeared. The crystalline form of prior art Form B changed after grinding. The results show that Form CS1 of present disclosure has better stability than prior art Form A and Form B under a certain mechanical pressure.

Example 4: Kinetic Solubility Comparison of Form CS1, Prior Art Form a and Form B Simulated gastrointestinal fluids such as FaSSIF (Fasted state simulated intestinal fluids) and FeSSIF (Fed state simulated intestinal fluids) are biorelevant media. Solubility in such media is close to in vivo solubility, because these media can reflect the effects of intestinal environment on drug release better.

A certain amount of Form CS1, prior art Form A and Form B were suspended in FaSSIF and FeSSIF to get saturated solutions. After equilibration for 4 h, concentrations (mg/mL) of the saturated solutions were measured by HPLC. The results are listed in Table 5.

TABLE 5

| Solid Form | Solubility (mg/mL) | |
|---|---|---|
|  | eSSIF | FaSSIF |
| Form CS1 | 74.8 | 75.3 |
| prior art Form A | 36.0 | 46.9 |
| prior art Form B | 29.2 | 52.0 |

The results show that the solubility of Form CS1 in the present disclosure is higher than that of prior art Form A and Form B.

Example 5: Morphology Comparison of Form CS1, Prior Art Form a and Form B

Figure 11:
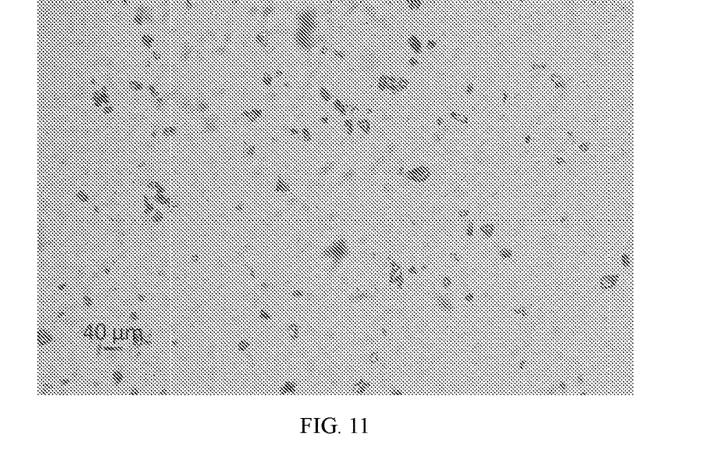
FIG. 11 shows a PLM plot of Form CS1.

According to paragraph [00179] of specification in WO2016205762A, Form A and Form B are needle-like crystals. Needle-like crystals are not beneficial to tableting because of poor compressibility and flowability. Furthermore, needle-like crystals usually carry static electricity, so it is difficult to form drug product. Morphology of Form CS1 of the present disclosure was checked by a polarizing microscope (PLM), and the PLM image is shown in FIG. 11. It shows that Form CS1 of the present disclosure is a spherical or short rod-like crystal instead of a needle-like crystal. Form CS1 has better flowability and is more suitable for processing and preparing drug product.

Example 6: Physical Stability of Form CS1 Under Different Pressures

A certain amount of Form CS1 were compressed into pellets under different pressures with suitable tableting die. Crystalline forms before and after tableting were checked by XRPD. The test results are shown in Table 6.

TABLE 6

Figure 12:
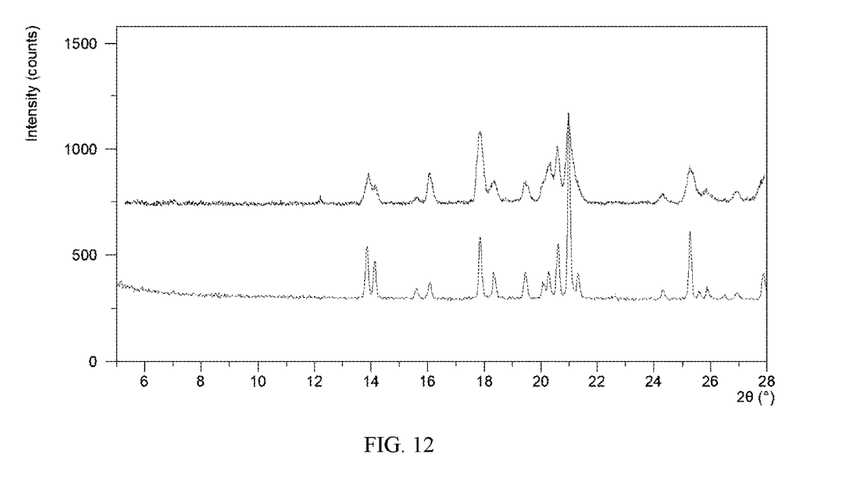
FIG. 12 shows an XRPD pattern overlay of Form CS1 before and after tableting under 3 kN (bottom: before tableting, top: after tableting).
Figure 13:
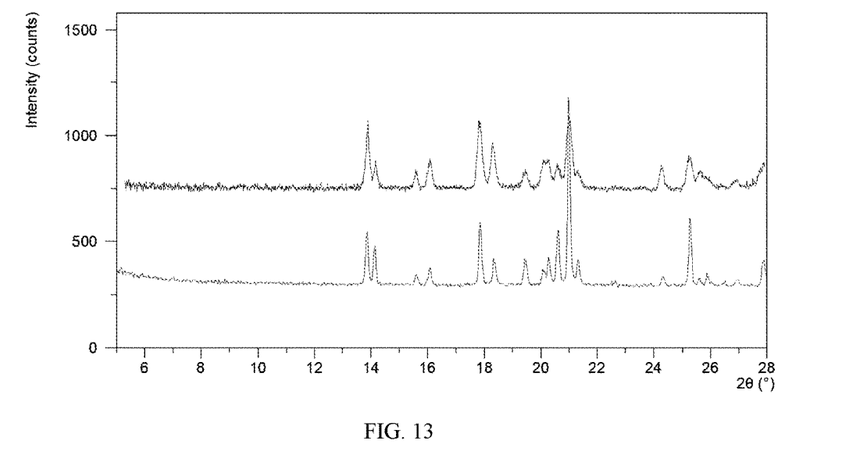
FIG. 13 shows an XRPD pattern overlay of Form CS1 before and after tableting under 7 kN (bottom: before tableting, top: after tableting).
Figure 14:
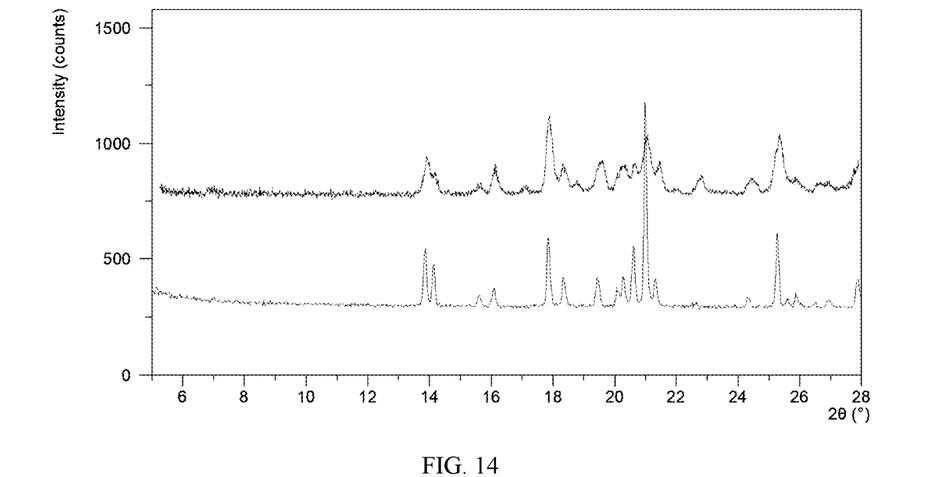
FIG. 14 shows an XRPD pattern overlay of Form CS1 before and after tableting under 14 kN (bottom: before tableting, top: after tableting).

| Before tableting | Pressure | After tableting |
|---|---|---|
| Form CS1 (FIG. 12, bottom) | 3 kN | Form CS1 (FIG. 12, top) |
| Form CS1 (FIG. 13, bottom) | 7 kN | Form CS1 (FIG. 13, top) |
| Form CS1 (FIG. 14, bottom) | 14 kN | Form CS1 (FIG. 14, top) |

The results show that Form CS1 has good stability under different pressures, which makes the process of drug product more reliable.

Example 7: Adhesiveness of Form CS1

30 mg of Form CS1 were weighed and then added into the dies of φ8 mm round tooling, compressed at 10 KN and held for 30s. The punch was weighed and the amount of material sticking to the punch was calculated. The compression was repeated twice and the cumulative amount, maximum amount and average amount of material sticking to the punch during the compression were recorded. Detailed experimental results are shown in Table 7, which indicates that Form CS1 has low adhesiveness.

TABLE 7

| Form | Maximum amount (mg) | Average amount (mg) | Cumulative amount (mg) |
|---|---|---|---|
| Form CS1 | 0.07 | 0* | 0* |

*No material stuck detected with sensitivity of existing method.

Example 8: Compressibility of Form CS1

A manual tablet press was used for compression. A certain amount of Form CS1 were added into the dies of round tooling and compressed at certain pressure manually, the tablet was stored in a desiccator for 24 h until complete elastic recovery. Hardness (H) was tested with an Intelligent Tablet Hardness Tester. Diameter (D) and thickness (L) were tested with a caliper. Tensile strength of the powder was calculated with the following formula: $T=2H/\pi DL$. Under a certain force, the greater the tensile strength, the better the compressibility. The test was conducted with recommended parameters of Table 8, and the results are presented in Table 9, which indicate that Form CS1 has good compressibility.

TABLE 8

| Dies | Sample amount | Pressure |
|---|---|---|
| φ6 mm round tooling | 80 mg | 10 kN |

TABLE 9

| Form | Thickness (mm) | Diameter (mm) | Hardness (N) | Tensile strength (MPa) |
|---|---|---|---|---|
| CS1 | 2.40 | 6.95 | 27.3 | 1.04 |

Example 9: Preparation of Form CS1 Drug Product

Form CS1 and excipients were blended according to formulation in Table 10 and round tablets were prepared using an ENERPAC manual tablet press at 5±0.5 kN pressure with a φ7 mm round tooling.

TABLE 10

| | Component | Quantity (mg/unit) | Mass ratio (%) |
|---|---|---|---|
| Intragranular excipients | EB-1020 Form CS1 | 50.00 | 25.00 |
| | Microcrystalline Cellulose | 126.00 | 63.00 |
| | Crosslinked povidone | 16.00 | 8.00 |
| | Povidone | 6.00 | 3.00 |
| | Magnesium stearate | 1.00 | 0.50 |
| | Total | 199.00 | 99.50 |
| Extragranular excipients | Magnesium stearate | 1.00 | 0.50 |
| | Total | 200.00 | 100.00 |

The tablet was packed in an HDPE bottle and stored under 25° C./60% RH and 40° C./75% RH conditions. Crystalline form and impurity of the sample were tested to check the stability of Form CS1 drug product at the end of 1 month. The results indicate that Form CS1 drug product can keep stable under 25° C./60% RH and 40° C./75% RH for at least 1 month. Moreover, Form CS1 has little change in purity, indicating that Form CS1 has good stability.

TABLE 11

Physical stability of Form CS1 in drug product

| Sample | Condition | Time | crystalline form of API after storage |
|---|---|---|---|
| Tablet containing Form CS1 | 25° C./60% RH | 1 month | Form CS1 |
| | 40° C./75% RH | 1 month | Form CS1 |

TABLE 12

Chemical stability of Form CS1 in drug product

| Condition | Time | Initial purity | Final purity | Purity change |
|---|---|---|---|---|
| 25° C./60% RH | 1 month | 99.79% | 99.75% | 0.04% |
| 40° C./75% RH | 1 month | 99.79% | 99.54% | 0.25% |

Example 10: In Vitro Dissolution Profile of Form CS1 Drug Product

In vitro dissolution test was performed on Form CS1 drug product obtained from example 9. Dissolution method according to Chinese Pharmacopoeia 2015<0931> dissolution and drug release tests was used. The conditions are as follows:

Medium: pH 5.0 acetic acid buffer solution

Method: Paddle

Volume: 900 mL

Speed: 50 rpm

Temperature: 37° C.

Figure 15:
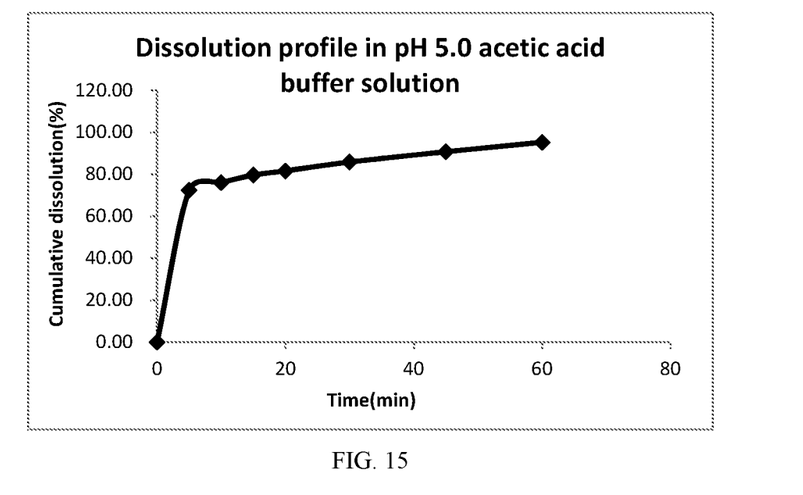
FIG. 15 shows an in vitro dissolution profile of Form CS1 drug product.

Dissolution results of Form CS1 drug product are presented in Table 13 and FIG. 15, which indicate that the drug product with Form CS1 as active ingredient has good dissolution.

TABLE 13

| Time (min) | Accumulative dissolution (%) Form CS1 drug product |
|---|---|
| 0 | 0.00 |
| 5 | 72.43 |
| 10 | 76.13 |
| 15 | 79.66 |
| 20 | 81.67 |
| 30 | 85.88 |
| 45 | 90.77 |
| 60 | 95.29 |

The examples described above are only for illustrating the technical concepts and features of the present disclosure, and intended to make those skilled in the art being able to understand the present disclosure and thereby implement it, and should not be concluded to limit the protective scope of the present disclosure. Any equivalent variations or modifications according to the spirit of the present disclosure should be covered by the protective scope of the present disclosure.

What is claimed is:

1. A crystalline form CS1 of compound I, wherein the X-ray powder diffraction pattern shows characteristic peaks at 2theta values of 21.0°±0.2°, 25.3°±0.2°, 14.1°±0.2°, 17.8°±0.2°, 20.6°±0.2°, and 16.1°±0.2°; and shows no characteristic peak at 2theta values of 12.3°±0.2° using CuKα radiation.

2. The crystalline form CS1 of compound I according to claim 1, wherein the X-ray powder diffraction pattern shows one or two characteristic peaks at 2theta values of 18.3°±0.2°, 19.4°±0.2° using CuKα radiation.

3. A process for preparing the crystalline form CS1 of compound I of claim 1,
wherein the process comprises:
Weighing a certain amount of compound I, melting by heating under an inert atmosphere, and cooling to obtain the crystalline form CS1.

4. The process according to claim 3, said heating and melting temperature is 248±2° C.

5. A pharmaceutical composition, said pharmaceutical composition comprises a therapeutically effective amount of crystalline form CS1 according to claim 1 and pharmaceutically acceptable carriers, diluents or excipients.

6. A method of treating attention deficit hyperactivity disorder, comprising administering to a subject in need thereof a therapeutically effective amount of crystalline Form CS1 according to claim 1.

7. A crystalline form CS1 of compound I, wherein the X-ray powder diffraction pattern shows characteristic peaks at 2theta values of 21.0°±0.2°, 25.3°±0.2°, 14.1°±0.2°, 17.8°±0.2°, 20.6°±0.2°, and 16.1°±0.2°; and shows no characteristic peak at 2theta values of 17.2°±0.2° using CuKα radiation.

8. The crystalline form CS1 of compound I according to claim 7, wherein the X-ray powder diffraction pattern shows one or two characteristic peaks at 2theta values of 18.3°±0.2°, 19.4°±0.2° using CuKα radiation.

9. A pharmaceutical composition, said pharmaceutical composition comprises a therapeutically effective amount of crystalline form CS1 according to claim 7 and pharmaceutically acceptable carriers, diluents or excipients.

10. A method of treating attention deficit hyperactivity disorder, comprising administering to a subject in need thereof a therapeutically effective amount of crystalline Form CS1 according to claim 7.

* * * * *